United States Patent [19]
Gusakov

[11] Patent Number: 5,782,761
[45] Date of Patent: Jul. 21, 1998

[54] MOLDED ELECTRODE

[75] Inventor: Ignaty Gusakov, East Aurora, N.Y.

[73] Assignee: Graphic Controls Corporation, Buffalo, N.Y.

[21] Appl. No.: 590,093

[22] Filed: Jan. 24, 1996

[51] Int. Cl.$^6$ .................................................. A61B 5/0416
[52] U.S. Cl. ........................... 600/391; 600/394; 600/395; 607/149
[58] Field of Search ........................... 128/639–643; 607/149, 152, 153; 600/372, 391, 392, 394, 395

[56] References Cited

U.S. PATENT DOCUMENTS

| | | |
|---|---|---|
| 2,660,175 | 11/1953 | Thrasher et al. ............ 128/643 |
| 3,474,775 | 10/1969 | Johnson ..................... 128/639 |
| 3,566,860 | 3/1971 | Moe, Jr. . |
| 3,606,881 | 9/1971 | Woodson . |
| 3,741,219 | 6/1973 | Sessions ..................... 607/153 |
| 4,050,453 | 9/1977 | Castillo et al. . |
| 4,082,087 | 4/1978 | Howson . |
| 4,352,359 | 10/1982 | Larimore et al. ............ 128/640 |
| 4,367,755 | 1/1983 | Bailey ....................... 607/152 |
| 4,370,984 | 2/1983 | Cartmell . |
| 4,442,315 | 4/1984 | Segawa . |
| 4,524,775 | 6/1985 | Rasmussen . |
| 4,633,879 | 1/1987 | Ong . |
| 4,646,747 | 3/1987 | Lundback ................... 128/643 |
| 4,685,467 | 8/1987 | Cartmell et al. . |
| 4,727,881 | 3/1988 | Craighead et al. .......... 128/641 |
| 4,742,828 | 5/1988 | Sundstrom . |
| 4,919,148 | 4/1990 | Muccio ...................... 607/152 |
| 4,938,219 | 7/1990 | Ishii et al. ................. 128/641 |
| 5,042,498 | 8/1991 | Dukes . |
| 5,222,498 | 6/1993 | Neward . |
| 5,261,402 | 11/1993 | DiSabito . |
| 5,330,527 | 7/1994 | Montecalvo et al. . |
| 5,345,935 | 9/1994 | Hirsch et al. ............... 128/643 |
| 5,356,428 | 10/1994 | Way . |
| 5,407,368 | 4/1995 | Strand et al. . |
| 5,427,096 | 6/1995 | Bogusiewicz et al. . |

*Primary Examiner*—Lee S. Cohen
*Attorney, Agent, or Firm*—Ratner & Prestia

[57] ABSTRACT

A conductive medical electrode formed from a moldable, conductive material such as carbon-filled plastic. In one embodiment, the electrode is an integral, conductive electrode including a stud adapted to detachably couple the electrode to a lead wire and a body integral with the stud. The body has a face disposed opposite the stud, for contacting a patient, which has a grooved pattern formed therein. The grooved pattern increases the surface area of the electrode in contact with a conductive adhesive and increases the conductivity between the patient and the electrode. A second embodiment features a two-piece, conductive electrode including an electrically conductive stud and an electrically conductive substrate having an opening formed therein and attached to the stud. The opening formed in the body creates a cavity which aids in retaining the conductive adhesive. The substrate has a face disposed opposite the stud, adapted to contact a patient, which has a grooved pattern formed therein. In a third embodiment, the conductive electrode includes a lead wire which is ultrasonically welded to the electrode body. Also provided is a method of manufacturing the integral, conductive electrode.

12 Claims, 4 Drawing Sheets

5,782,761

1

MOLDED ELECTRODE

BACKGROUND OF THE INVENTION

1. Field of the Invention

The present invention relates to medical electrodes that are used with a conductive adhesive and, in particular, to medical electrodes having a grooved pattern on a patient-contacting face that increases the surface area of the electrode in contact with the conductive adhesive.

2. Description of the Related Art

Medical electrodes are often used to monitor heart activity of a patient such as in electrocardiograph (ECG) applications. ECG electrode applications often require use of electrodes that are radiolucent to allow for continuous monitoring of the patient while x-ray or nuclear magnetic resonance (NMR) imaging is performed. Current radiolucent electrodes, like the Graphic Controls 2525 electrode and the ConMed ClearTrace electrode, have components that are made from carbonfilled plastics such as polyurethane, polyethylene, or acrylonitrile-butadiene-styrene (ABS) copolymer. Metals are eliminated because they will show-up on x-rays, whereas carbon does not show up at normal x-ray dose levels.

Generally, an ECG electrode is made with a substrate material upon which other components are mounted. These other components include a stud and an eyelet that attaches the electrode to a wire coupled to an external monitor. Carbon-filled studs and eyelets cost more than the non-radiolucent metal varieties, are more difficult to assemble, often crack after joining by compression, experience a higher scrap rate due to production rejects, and are not as conductive as metal versions. To enhance conductivity, a silver/silver chloride coating is applied to the eyelet that is in contact with a conductive, adhesive gel that attaches the electrode to the patient. The silver/silver chloride coating enhances conductivity as well as other properties such as defibrillation recovery and DC offset, but increases costs due to the cost of the raw material and the cost of applying the silver/silver chloride coating to the electrode.

SUMMARY OF THE INVENTION

The present invention is a conductive medical electrode that can replace both conventional radiolucent electrodes and non-radiolucent electrodes. Unlike conventional electrodes that are assembled with various parts using automated machinery extensively, assembly of the electrode involves a small number of steps. The major part of the electrode that replaces the substrate, stud, and eyelet in conventional electrodes is made in one piece by a molding process. The electrode may be formed from a moldable, conductive material such as carbon-filled plastic.

A first embodiment of the invention is an integral, conductive electrode including a stud adapted to detachably couple the electrode to a lead wire and a body integral with the stud. The body has a face disposed opposite the stud, for contacting a patient, which has a grooved pattern formed therein. The grooved pattern increases the surface area of the electrode in contact with the conductive adhesive and increases the conductivity between the patient and the electrode.

A second embodiment of the invention is a two-piece, conductive electrode including an electrically conductive stud adapted to detachably couple the electrode to a lead wire and an electrically conductive substrate having an opening formed therein and attached to the stud. The opening formed in the substrate creates a cavity which aids in retaining a conductive adhesive. The substrate has a face disposed opposite the stud, for contacting a patient, which has a grooved pattern formed therein.

In a third embodiment of the invention, the conductive electrode comprises an electrically conductive body having a face, for contacting a patient, which has a grooved pattern formed therein. A lead wire is ultrasonically welded to the electrode body.

DETAILED DESCRIPTION OF THE INVENTION

Figure 1:
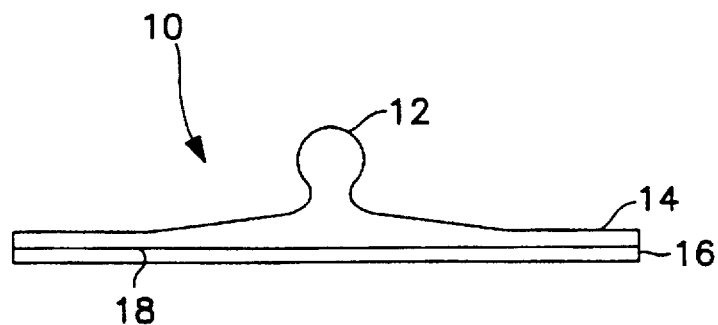
FIG. 1 is a side view of an exemplary electrode in accordance with a first embodiment of the invention.

FIG. 1 shows the conductive electrode 10 according to a first embodiment of the invention. The electrode 10 includes a stud 12 integral with a body 14. The stud 12 and the body 14 are integrally formed in a molding process using conductive plastic. A lead wire with a conventional snap attachment (not shown) may be connected to the stud 12. The portion of the body 14 away from the stud 12 is thin and pliable, allowing the electrode 10 to conform to the contours of a patient. The flat face 18 of the electrode 10 is coated with a conductive adhesive 16. The conductive adhesive 16 may be a pressure-sensitive adhesive or a conductive, adhesive gel. The conductive adhesive 16 attaches the electrode 10 to the patient and conducts electrical signals to and from the patient.

Figure 2:
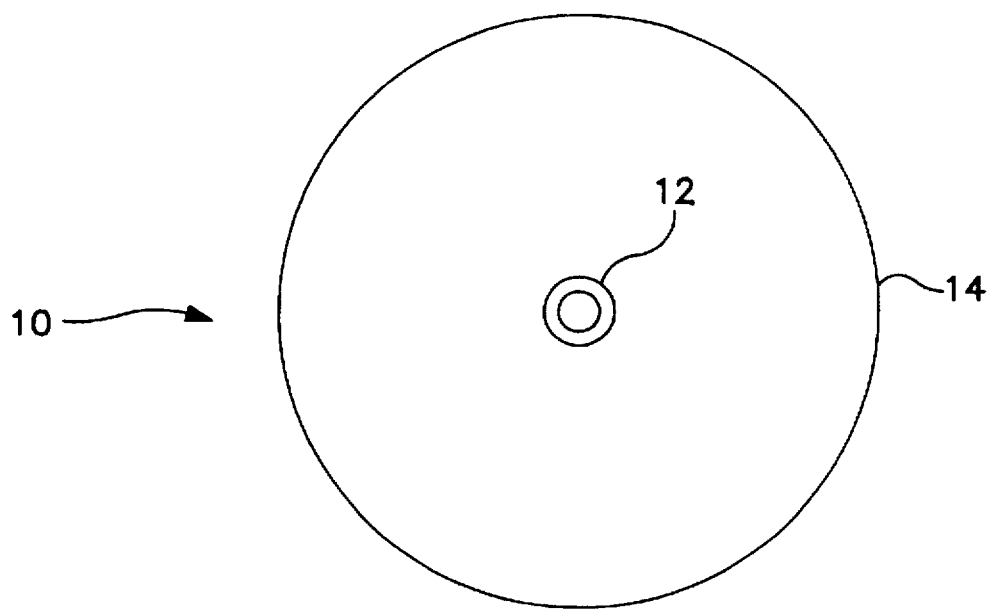
FIG. 2 is top view of the electrode shown in FIG. 1.

FIG. 2 is a top view of the electrode shown in FIG. 1. The electrode body 14 has a large area so that the conductivity of the electrode 10 is significantly greater than that available with eyelets alone. The dimension of the electrode body 14 is significantly greater than the dimension of stud 12. In an exemplary embodiment, stud 12 has a diameter of 3.92 millimeters and body 14 has a diameter of 36.5 millimeters. This feature eliminates, in part, the need for a silver/silver chloride coating on the electrode 10. The electrode body 14 may be a variety of shapes such as oval, rectangular, square, or triangular as well as circular.

Figure 3A:
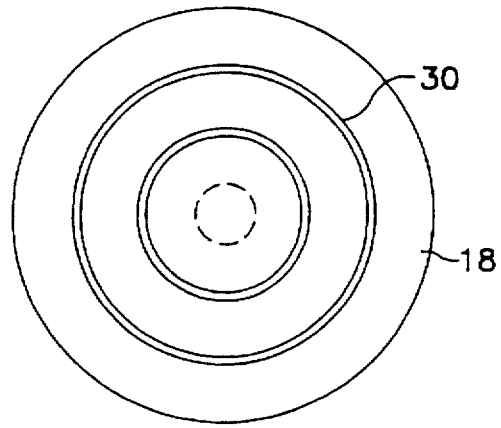
FIGS. 3A through 3F illustrate grooved patterns that may be formed on the bottom of th electrode shown in FIG. 1.
Figure 3D:
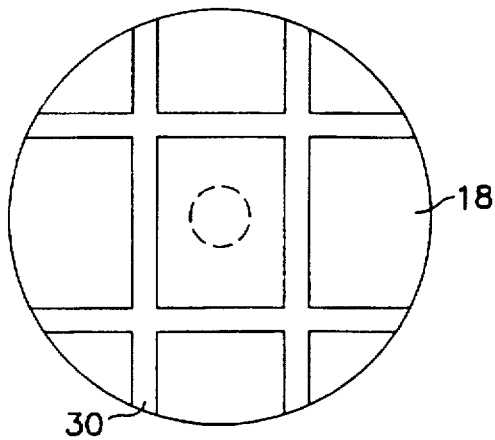
Figure 3B:
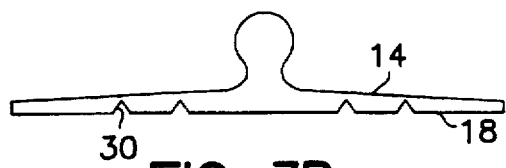
Figure 3E:
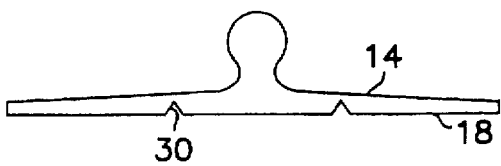
Figure 3C:
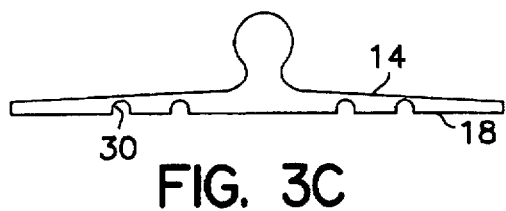
Figure 3F:
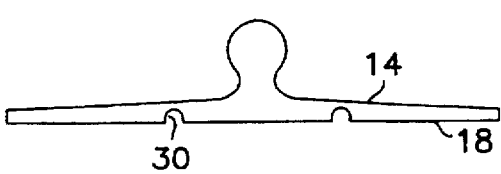

As shown in FIGS. 3A and 3B, to further enhance conductivity, the flat face 18 of the body 14 contains a grooved pattern 30 to increase the surface area of the flat face 18 in contact with the conductive adhesive 16 (shown in FIG. 1). FIG. 3 A illustrates a concentric pattern of grooves 30 which may be V-shaped as shown in FIG. 3B or curved as shown in FIG. 3C. FIG. 3D illustrates a checkerboard pattern of grooves 30 which also may be V-shaped or curved as shown in FIGS. 3E and 3F, respectively. For ease of illustration, FIGS. 3A–3F show a limited number of spaced grooves 30 formed on the flat face 18. It is understood that a large number of grooves 30 may be formed in the flat face 18 and that adjacent grooves 30 may be in close proximity to each other. It is also understood that a variety of groove patterns and groove profiles may be used to increase the surface area of the flat face 18 in contact with the conductive adhesive 16.

The electrode 10 shown in FIG. 1 may be made from carbon-filled plastics such as polyurethane, polyethylene, or acrylonitrile-butadiene-styrene (ABS) copolymer. The carbon-filled plastic may be radiolucent or non-radiolucent. A variety of molding processes may be used to manufacture the electrode 10, including injection molding, casting-type molding, thermal forming, and compression molding. For example, in injection molding the carbon-filled plastic is heated to a fluid state and forced under pressure through a runner system into a closed mold. The electrode 10 is removed once the carbon-filled plastic has cooled and solidified. The mold includes ridges that form a grooved pattern, such as those shown in FIGS. 3A through 3F. In this way, the entire electrode 10 is formed in a single molding step which reduces costs. In addition, the reduction in the number of parts forming the electrode 10 reduces the scrap rate during manufacture.

Figure 4:
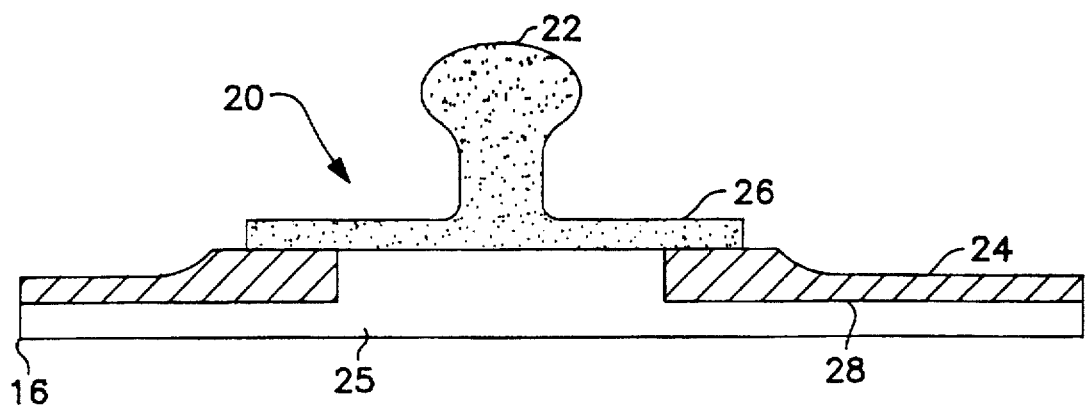
FIG. 4 is a side view of an exemplary electrode in accordance with a second embodiment the invention.

FIG. 4 illustrates a second embodiment of the present invention. Electrode 20 includes a stud 22 integral with a base 26. The stud 22 and the base 26 are made from a conductive plastic and formed through a molding process such as injection molding. Of course, other molding techniques may be used as discussed above. The base 26 is heat sealed to a substrate 24 which is also made from a conductive plastic. Substrate 24 is similar to the body 14 (shown in FIG. 1) and includes a thin, pliable region away from the base 26 which allows the electrode 20 to conform to the contours of a patient. The outer dimension of the substrate 24 is larger than the outer dimension of the stud 22 to provide a large surface area in contact with the patient. Substrate 24 has a hole 25 formed therein. The base 26 completely overlaps the hole 25 and forms a cavity which assists in retaining the conductive adhesive 16. The face 28 of the substrate 24 includes a grooved pattern, such as those shown in FIGS. 3A through 3F.

Figure 5:
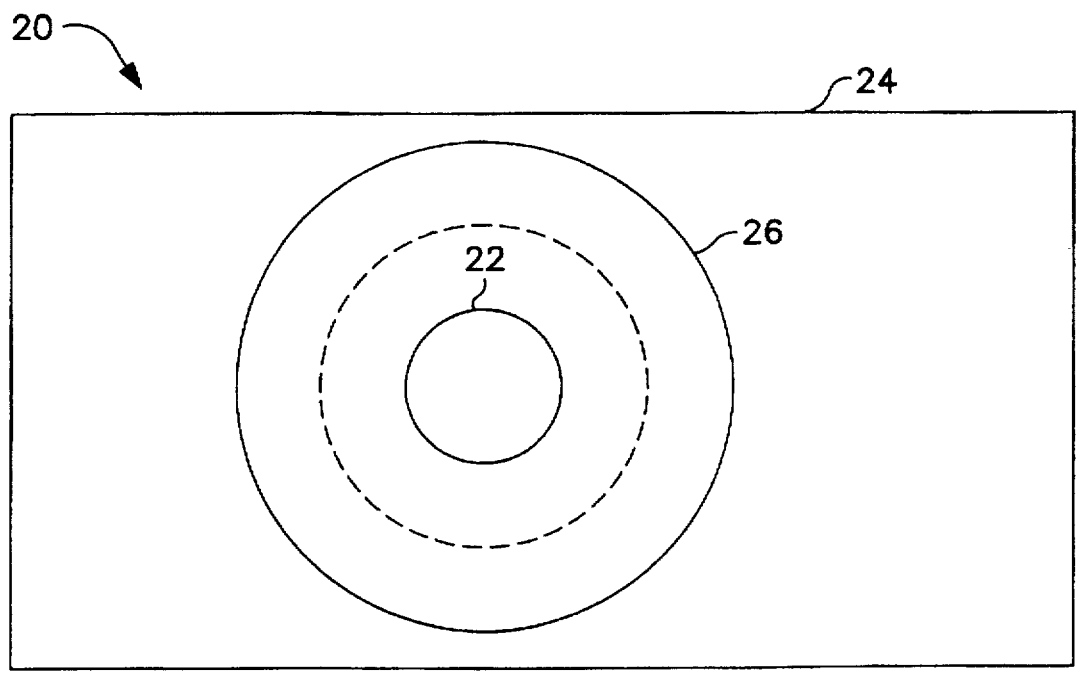
FIG. 5 is a top view of the electrode shown in FIG. 4.

FIG. 5 illustrates a top view of the electrode 20 shown in FIG. 4. The substrate 24 may be any shape and is shown in FIG. 5 as rectangular. This allows the shape of the substrate 24 to be altered without changing the mold for the stud 22 and the base 26. To customize the electrode 20, only a new substrate 24 needs to be formed and heat sealed to base 26. Thus, the manufacturer can customize the electrode 20 to a user's needs without incurring large costs.

Figure 6:
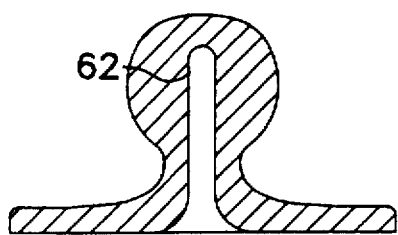
FIG. 6 is a side view of a variation of the electrode stud shown in FIGS. 1 and 4.

FIG. 6 illustrates a variation of the stud 12 shown in FIG. 1 or the stud 22 shown in FIG. 4. The stud 12 or the stud 22 includes a hollow region 62 that provides for material relief. Of course, this variation requires a more complex mold to manufacture.

Figure 7:
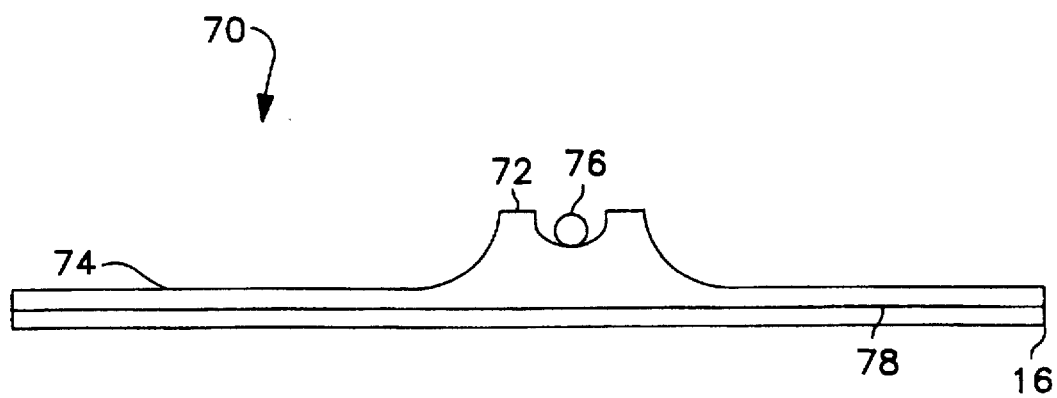
FIG. 7 is view of an exemplary electrode in accordance with a third embodiment of the invention.

FIG. 7 illustrates a third embodiment of the present invention. The electrode 70 includes a weld area 72 integral with a body 74. The weld area 72 and body 74 are made from conductive plastic and are formed through a molding process such as injection molding. Of course, other molding techniques may be used as discussed above. Body 74 is similar to body 14 (shown in FIG. 1) and includes a thin, pliable region away from weld area 72 which allows the electrode 70 to conform to the contours of a patient. The face 78 of the body 74 includes a grooved pattern, such as those shown in FIGS. 3A through 3F. The weld area 72 receives a lead wire 76 which is made of copper or carbon strands. The lead wire 76 is ultrasonically welded to weld area 72. A conductive adhesive 16 is applied to the bottom of the face 78 to attach the electrode 70 to the patient's skin and conduct electrical signals to and from the patient.

It will be understood by one skilled in the art that many variations of the embodiments described herein are contemplated. Although the invention has been described in terms of exemplary embodiments, it is contemplated that it may be practiced as outlined above with modifications within the spirit and scope of the appended claims.

What is claimed:

1. An integral, conductive electrode comprising:

a one-piece component having an electrically conductive stud adapted to detachably couple the electrode to a lead wire and an electrically conductive body integral with said stud, said body having a face disposed opposite said stud with a surface area and a furrow pattern formed therein; and a conductive adhesive disposed on said face of said body and adapted to contact a patient, said furrow pattern of said face increasing said surface area of said face of said body in contact with said conductive adhesive and increasing the conductivity between said body and said conductive adhesive.

2. The integral, conductive electrode of claim 1, wherein said stud and said body are made from conductive plastic.

3. The integral, conductive electrode of claim 2, wherein said conductive plastic is carbon-filled plastic.

4. The integral, conductive electrode of claim 3, wherein said carbonfilled plastic is radiolucent.

5. The integral, conductive electrode of claim 3, wherein said plastic is selected from the group consisting of polyurethane, polyethylene, and acrylonitrilebutadiene-styrene.

6. The integral, conductive electrode of claim 1, wherein said body includes a flat, thin, pliable region adapted to conform to the contours of the patient.

7. The integral, conductive electrode of claim 1, wherein said stud has a first radius and said body has a second radius significantly greater than the first radius.

8. The integral, conductive electrode of claim 1, further comprising a conductive, pressure-sensitive adhesive coated on said face.

9. The integral, conductive electrode of claim 1, further comprising a conductive gel coated on said face.

10. The integral, conductive electrode of claim 9, wherein said gel is adhesive.

11. The integral, conductive electrode of claim 1, wherein said stud includes a hollow providing material relief.

12. An electrode comprising:

a one-piece component having an electrically conductive contact portion adapted to couple the electrode to a lead wire and an electrically conductive body adjacent to and integral with said contact portion, said body having a face disposed opposite said contact portion with a surface area and a furrow pattern formed therein; and a conductive adhesive disposed on said face of said body and adapted to contact a patient, said furrow pattern of said face increasing said surface area of said face of said body in contact with said conductive adhesive and increasing the conductivity between said body and said conductive adhesive.

\* \* \* \* \*